United States Patent
Cheng et al.

(10) Patent No.: US 9,829,415 B2
(45) Date of Patent: Nov. 28, 2017

(54) METROLOGY SAMPLING METHOD AND COMPUTER PROGRAM PRODUCT THEREOF

(71) Applicant: NATIONAL CHENG KUNG UNIVERSITY, Tainan (TW)

(72) Inventors: Fan-Tien Cheng, Tainan (TW); Chun-Fang Chen, Tainan (TW); Hsuan-Heng Huang, Tainan (TW); Chu-Chieh Wu, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 374 days.

(21) Appl. No.: 14/666,324

(22) Filed: Mar. 24, 2015

(65) Prior Publication Data
US 2015/0276558 A1    Oct. 1, 2015

(30) Foreign Application Priority Data

Mar. 26, 2014   (TW) .............................. 103111289 A (51) Int. Cl.
*G06F 15/18* (2006.01)
*G01N 1/00* (2006.01)
(Continued)

(52) U.S. Cl.
CPC ......... *G01N 1/00* (2013.01); *G05B 19/41875* (2013.01); *G06F 17/11* (2013.01); *G05B 2219/45031* (2013.01)

(58) Field of Classification Search
None
See application file for complete search history.

(56) References Cited

U.S. PATENT DOCUMENTS 8,095,484 B2    1/2012  Cheng et al.
2009/0292386 A1*  11/2009  Cheng .............. G05B 19/41875
                                                    700/109
(Continued)

FOREIGN PATENT DOCUMENTS

| CN | 103513159 A | 1/2014 |
| TW | I267012 B | 11/2006 |
| TW | 200745895 A | 12/2007 |

OTHER PUBLICATIONS

D. Kurz, et. al., "Monitoring virtual metrology reliability in a sampling decision system," Automation Science and Engineering (CASE), 2013 IEEE International Conference; Aug. 17-20, 2013; p. 20-25.*

(Continued)

*Primary Examiner* — Charles Garber
*Assistant Examiner* — Alia Sabur
(74) *Attorney, Agent, or Firm* — CKC & Partners Co., Ltd.

(57) ABSTRACT

In a metrology sampling method, various index values that can detect various status changes of a process tool (such as maintenance operation, parts changing, parameter adjustment, etc.), and/or information abnormalities of the process tool (such as abnormal process data, parameter drift/shift, abnormal metrology data, etc.) appear in a manufacturing process are applied to develop an intelligent sampling decision (ISD) scheme for reducing sampling rate while VM accuracy is still sustained. The indices includes a reliance Index (RI), a global similarity index (GSI), a process data quality index ($DQI_X$) and a metrology data quality index ($DQI_Y$).

16 Claims, 5 Drawing Sheets

(51) Int. Cl.
    *G05B 19/418* (2006.01)
    *G06F 17/11* (2006.01)

(56) References Cited

U.S. PATENT DOCUMENTS

2012/0029662 A1* 2/2012 Cheng .................. G05B 13/042
                                                    700/29
2013/0257461 A1  10/2013 Heidmann

OTHER PUBLICATIONS

Jae Yeon Claire Baek, Costas J. Spanos, "Optimization of blended virtual and actual metrology schemes," Proc. SPIE 8324, Metrology, Inspection, and Process Control for Microlithography XXVI, 83241K (Apr. 5, 2012).*

D. Kurz, C. De Luca and J. Pilz, "A Sampling Decision System for Virtual Metrology in Semiconductor Manufacturing," in IEEE Transactions on Automation Science and Engineering, vol. 12, No. 1, pp. 75-83, Jan. 2015.*

C. Yugma, J. Blue, S. Sauzere-Peres, A. Obeid, "Integration of scheduling and advanced process control in semiconductor manufacturing: review and outlook," J. Sched. (2015) 18:195-205.*

D. Kurz, C. DeLuca and J. Pilz, "Sampling Decision System in semiconductor manufacturing using Virtual Metrology," 2012 IEEE International Conference on Automation Science and Engineering (CASE), Seoul, 2012, pp. 74-79.*

C. F.Chen, F. T. Cheng, C. C. Wu and H. H. Huang, "Preliminary study of an intelligent sampling decision scheme for the AVM system," 2014 IEEE International Conference on Robotics and Automation (ICRA), Hong Kong, 2014, pp. 3496-3501.*

Bousetta, A., and A. J. Cross., "Adaptive Sampling Methodology for In-Line Defect Inspection." In Proceedings of IEEE, SEMI Advanced Semiconductor Manufacturing Conference, 25-31. Munich: IEEE, Apr. 11-12, 2005.

Chien, C.-F., K.-H. Chang, and C.-P. Chen., "Design of a Sampling Strategy for Measuring and Compensating for Overlay Errors in Semiconductor Manufacturing." International Journal of Production Research, vol. 41, No. 11, pp. 2547-2561, 2003.

André Holfeld et al., "A Fab-wide APC Sampling Application." IEEE Transactions on Semiconductor Manufacturing, vol. 20, No. 4, pp. 393-399, Nov. 2007.

Daniel Kurz et al., "Sampling Decision System in semiconductor manufacturing using Virtual Metrology" In Proceedings of 2012 IEEE International Conference on Automation Science and Engineering (CASE 2012), 74-79. Seoul: IEEE, Aug. 20-24, 2012.

Daniel Kurz et al., "Monitoring Virtual Metrology Reliability in a Sampling Decision System." In Proceedings of 2013 IEEE International Conference on Automation Science and Engineering (CASE 2013), 20-25. Madison, WI: IEEE, Aug. 17-21, 2013.

Lee, J. H., "Artificial intelligence-based sampling planning system for dynamic manufacturing process." Expert System with Applications, 22:117-133, 2002.

Justin Nduhura-Munga et al.,"Dynamic Management of Controls in Semiconductor Manufacturing." In Proceedings of IEEE/SEMI Advanced Semiconductor Manufacturing Conference, 1-6. Saratoga Springs, NY: IEEE/SEMI, May 16-18, 2011.

Justin Nduhura-Munga et al., "A Literature Review on Sampling Techniques in Semiconductor Manufacturing." IEEE Transactions on Semiconductor Manufacturing, vol. 26, No. 2, pp. 188-195, May 2013.

Alan Weber, "Virtual Metrology and Your Technology Watch List: Ten Things You Should Know about This Emerging Technology." Future Fab International, Issue 22, Section 4, pp. 52-54, 2007.

* cited by examiner

METROLOGY SAMPLING METHOD AND COMPUTER PROGRAM PRODUCT THEREOF

RELATED APPLICATIONS

This application claims priority to Taiwan Application Serial Number 103111289, filed Mar. 26, 2014, which is herein incorporated by reference.

BACKGROUND

Field of Invention

The present invention relates to a metrology sampling method. More particularly, the present invention relates to a metrology sampling method for reducing a sampling rate.

Description of Related Art

Nowadays, most of the semiconductor and TFT-LCD plants adopt sampling test methods to monitor the quality of each product or workpiece (i.e. "wafer" in IC foundries or "glass" in TFT-LCD factories) processed by process tools. In general, after each N (for example, 25) workpieces are processed by the process tool, a manufacturing system designates the $N^{th}$ workpiece in the each N workpieces as a workpiece expected (scheduled) to be measured, i.e. the sampling rate is 1/N. The workpiece expected to be measured then will be sent to a metrology tool for measurement, thereby inspecting the production quality of the process tool. This conventional sampling method is based on the presupposition that no abnormal circumstances will abruptly occur in the production processes, and thus the measurement result of the sampled product or workpiece can be used to determine the quality of the workpieces in the same lot with the sampled workpiece. Because the measurement time and tool required by the real workpiece metrology result in the increase of cycle time and production cost. Therefore, reducing the sampling rate to as low as possible is an important task for manufactures for reducing cycle time and production cost.

On the other hand, virtual metrology (VM) can be used to lower the frequency of actual measurement on workpiece to reduce the sampling rate. However, if a production variation occurs on the workpiece which is planned for measurement, no real metrology is available during this period for updating the VM models, thus resulting in poor VM prediction accuracy. Therefore, how to sample and obtain an appropriate workpiece in time affects the prediction accuracy of VM models.

Hence, there is a need to provide a metrology sampling method for overcoming the aforementioned shortcomings of the conventional skill.

SUMMARY

An object of the present invention is to provide a metrology sampling method for reducing a metrology sampling for workpieces.

Another object of the present invention is to provide a metrology sampling method for providing an actual measurement value of a workpiece in time to retuning or retraining a VM model, thereby assuring VM accuracy.

According to the aforementioned objects, a metrology sampling method is provided, in this metrology sampling method, at first, a plurality of sets of historical process data used by a process tool for processing historical workpieces are collected. Then, a model-creation step is performed. In the model-creation step, the sets of historical process data are used to build a $DQI_X$ (Process Data Quality Index) model and a GSI (Global Similarity Index) model and compute a $DQI_X$ threshold and a GSI threshold. Thereafter, a metrology workpiece sampling step is performed. In the metrology workpiece sampling step, a workpiece is provided to the process tool, in which the process tool has a set of process data for processing the workpiece. Then, the set of process data is inputted into the $DQI_X$ model and the GSI model, thereby obtaining a $DQI_X$ value and a GSI value of the set of process data of the workpiece. When the $DQI_X$ value of the workpiece is greater than the $DQI_X$ threshold, a measurement of the workpiece is skipped. When the $DQI_X$ value of the workpiece is smaller than or equal to the $DQI_X$ threshold, a step is performed to check if the workpiece is a workpiece expected to be measured, thereby obtaining a first checking result. When the first checking result is true, metrology is performed on the workpiece. When the first checking result is false, a step is performed to check if the GSI value of the workpiece is smaller than or equal to the GSI threshold, thereby obtaining a second checking result. When the second checking result is true, the measurement of the workpiece is skipped.

According to the aforementioned objects, another metrology sampling method is provided. In the metrology sampling method, a predetermined workpiece sampling rate 1/N is assigned, in which the predetermined workpiece sampling rate is directed to selecting the $N^{th}$ workpiece in each N workpieces processed by a process tool as a workpiece expected to be measured. In a metrology workpiece sampling step of the metrology sampling method, a workpiece count is increased by 1. Then, a first checking step is performed to check if the $DQI_X$ value is smaller than or equal to the $DQI_X$ threshold, thereby obtaining a first checking result. When the first checking result is false, a measurement of the workpiece is skipped. When the first checking result is true, a second checking step is performed to check if the workpiece count is greater than or equal to N, thereby obtaining a second checking result. When the second checking result is true, metrology is performed on the workpiece and the workpiece count is set to 0. When the second checking result is false, a third checking step is performed to check if the GSI value of the workpiece is smaller than or equal to the GSI threshold, thereby obtaining a third checking result. When the third checking result is true, the measurement of the workpiece is skipped.

According to the aforementioned objects, a computer program product stored on a non-transitory tangible computer readable recording medium is provided. When the computer program product is loaded by a computer and executed, the aforementioned metrology sampling methods are performed.

Thus, with the application of the embodiments of the present invention, the workpiece sampling rate can be greatly lowered, and the VM accuracy can be effectively assured.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

Reference will now be made in detail to the present embodiments of the invention, examples of which are illustrated in the accompanying drawings. Wherever possible, the same reference numbers are used in the drawings and the description to refer to the same or like parts.

Embodiments of the present invention apply various indices to develop an Intelligent Sampling Decision (ISD) scheme, in which those indices can be used to detect various process-related status changes of a process tool during production (such as preventive-maintenance (PM) operation, process-tool malfunction, recipe change, etc.), or information of abnormality of the process tool (such as poor process data quality, deviation (shift or drift) of process data, poor metrology data quality, etc.). The indices includes a reliance Index (RI), a global similarity index (GSI), a process data quality index ($DQI_X$) and a metrology data quality index ($DQI_y$). The RI value, the GSI value, the $DQI_X$ value and the $DQI_y$ value used in the embodiments of the present invention can be referenced to U.S. Pat. No. 8,095,484 B2. Embodiments of the present invention can be combined with the VM system disclosed by U.S. Pat. No. 8,095,484 B2. U.S. Pat. No. 8,095,484 B2 is hereby incorporated by reference. The RI value is designed to gauge the reliance level of a virtual metrology value. The GSI value is used to assess the degree of similarity between the current set of input process data and all of the sets of process data used for building and training a conjecture model. The GSI value is provided to help the RI value gauge the reliance level of VM system. The $DQI_X$ value is used to evaluate whether a set of process data used for producing a workpiece is abnormal, and the $DQI_y$ value is used to evaluate whether the metrology data of the workpiece are abnormal.

Hereinafter, theoretical bases related to the RI value (RI model), the GSI value (GSI model), the $DQI_X$ value ($DQI_X$ model) and the $DQI_y$ value ($DQI_y$ model) are first explained.

The RI and GSI are used to learn in real time whether the VM value is reliable. The RI model is used to compute a RI value between 0 and 1 by analyzing the process data of the process tool, thereby determining whether the virtual metrology result can be trusted. The GSI model is used to compute the GSI value for the process. The GSI value is defined as the degree of similarity between the current set of input process data and all of the sets of the process data used for building or training the models.

Referring to Table 1, n sets of historical data are assumed to be collected, including process data ($X_i$, i=1, 2, . . . , n) and the corresponding actual measurement values ($y_i$, i=1, 2, . . . , n), where each set of process data contains p individual parameters (from parameter 1 to parameter p), namely $X_i=[x_{i,1}, x_{i,2}, \ldots, x_{i,p}]^T$. Additionally, (m-n) sets of process data in actual production were also collected, but no actual measurement values are available besides $y_{n+1}$. That is, only the first among (m-n) pieces of the products is selected and actually measured. In the current manufacturing practice, the actual measurement value $y_{n+1}$ obtained is used to infer and evaluate the quality of the (m−n−1) pieces of the products.

TABLE 1

| Sample Data Set | Parameter 1 | Parameter 2 | | Parameter p | Actual Measurement Value |
|---|---|---|---|---|---|
| 1 | $x_{1,1}$ | $x_{1,2}$ | . . . | $x_{1,p}$ | $y_1$ |
| 2 | $x_{2,1}$ | $x_{2,2}$ | . . . | $x_{2,p}$ | $y_2$ |
| . . . | . . . | . . . | . . . . . . | . . . | . . . |
| n | $x_{n,1}$ | $x_{n,2}$ | . . . | $x_{n,p}$ | $y_n$ |
| n + 1 | $x_{n+1,1}$ | $x_{n+1,2}$ | . . . | $x_{n+1,p}$ | $y_{n+1}$ |
| n + 2 | $x_{n+2,1}$ | $x_{n+2,2}$ | . . . | $x_{n+2,p}$ | Zip |
| . . . | . . . | . . . | . . . . . . | . . . | . . . |
| m | $x_{m,1}$ | $x_{m,2}$ | . . . | $x_{m,p}$ | Zip |

As shown in Table 1, $y_1, y_2, \ldots, y_n$ are historical measurement values, and $y_{n+1}$ is the actual measurement value of the first piece of the products being manufactured. Generally, a set of actual measurement values ($y_i$, i=1, 2, . . . , n) is a normal distribution with mean μ and standard deviation σ, namely $y_i \sim N(\mu, \sigma^2)$.

All the actual measurement values can be standardized in terms of the mean and standard deviation of the sample set ($y_i$, i=1, 2, . . . , n). Their standardized values (also called z scores) $Z_{y_1}, Z_{y_2}, \ldots Z_{y_n}$ are thus derived, where each z score has mean zero and standard deviation one, namely $Z_{y_i} \sim N(0, 1)$. Regarding the actual measurement data, a corresponding $Z_{y_i}$ close to 0 indicates that the actual measurement value approaches the central value of the specification. The equations for standardization are listed as follows:

$$Z_{y_i} = \frac{y_i - \bar{y}}{\sigma_y}, i = 1, 2, \ldots, n \quad (1)$$

$$\bar{y} = \frac{1}{n}(y_1 + y_2 + \ldots + y_n) \quad (2)$$

$$\sigma_y = \sqrt{\frac{1}{n-1}[(y_1 - \bar{y})^2 + (y_2 - \bar{y})^2 + \ldots + (y_n - \bar{y})^2]} \quad (3)$$

wherein
$y_i$ is the i-th actual measurement value,
$Z_{y_i}$ is the standardized i-th actual measurement value,
$\bar{y}$ is the mean of all the actual measurement values, and
$\sigma_y$ is the standard deviation of all the actual measurement values.

The explanation herein adopts a neural-network (NN) algorithm as the conjecture algorithm for establishing the conjecture model performing virtual measurement, and uses such as a multi-regression (MR) algorithm to be the reference algorithm for establishing the reference model that serves as a comparison base for the conjecture model. However, the present invention can also apply other algorithms to be the conjecture algorithm or the reference algorithm, such as a back propagation neural network (BPNN) algorithm, a general regression neural network (GRNN) algorithm, a radial basis function neural network (RBFNN) algorithm, a simple recurrent network (SRN) algorithm, a support vector data description (SVDD) algorithm, a support vector machine (SVM) algorithm, a multiple regression (MR) algorithm, a partial least squares (PLS) algorithm, a nonlinear iterative partial least squares (NIPALS) algorithm or generalized linear models (GLMs), provided the reference algorithm differs from the conjecture algorithm, such as a SVM algorithm and other related algorithms, and thus the present invention is not limited thereto.

When the NN and MR algorithms are utilized, if their convergence conditions both are that SSE (Sum of Square Error) is minimized with $n \to \infty$, their standardized predictive measurement values (defined as $Z_{\hat{y}_{Ni}}$ and $Z_{\hat{y}_{ri}}$ respectively) should be the same as the standardized actual measurement value $Z_{y_i}$. Restated, when $n \to \infty$, $Z_{y_i} = Z_{\hat{y}_{Ni}} = Z_{\hat{y}_{ri}}$ all represent the standardized actual measurement value, but they have different names due to having different purposes and different estimating models. Hence, $Z_{\hat{y}_{Ni}} \sim N(\mu_{Z_{yi}}, \sigma_{Z_y}^2)$ and $Z_{\hat{y}_{ri}} \sim (\mu_{Z_{yi}}, \sigma_{Z_y}^2)$ indicate that $Z_{\hat{y}_{Ni}}$ and $Z_{\hat{y}_{ri}}$ share the same statistical distribution. However, owing to the existence of different estimating models, the estimations of mean and standard deviation differ between those two prediction algorithms. Namely the standardized mean-estimating equation $(\hat{\mu} = Z_{\hat{y}_{Ni}})$ and standard-deviation-estimating equation $$(\hat{\sigma}_{Z_y} = \hat{\sigma}_{Z_{\hat{y}_N}})$$

with respect to the NN conjecture model differ from the standardized mean-estimating equation $$(\hat{\mu}_{Z_{yi}} = Z_{\hat{y}_{ri}})$$

and standard-deviation-estimating equation $$(\hat{\sigma}_{Z_y} = \hat{\sigma}_{Z_{\hat{y}_r}})$$

with respect to the MR reference model.

The RI is designed to gauge the reliance level of the virtual metrology value. The RI thus should consider the degree of similarity between the statistical distribution $Z_{\hat{y}_N}$ of the virtual metrology value and the statistical distribution $Z_{y_i}$ of the actual measurement value. However, when virtual metrology is applied, no actual measurement value can be used to verify the trustworthiness of the virtual metrology value. (Notably, virtual metrology becomes unnecessary if actual measurement values are obtained.) Instead, the present invention adopts the statistical distribution $Z_{\hat{y}_r}$ estimated by the reference algorithm which is such as the MR algorithm to replace $Z_{y_i}$. The reference algorithm also can be such as a time-series algorithm and other related algorithms, and thus the present invention is not limited thereto.

Figure 1:
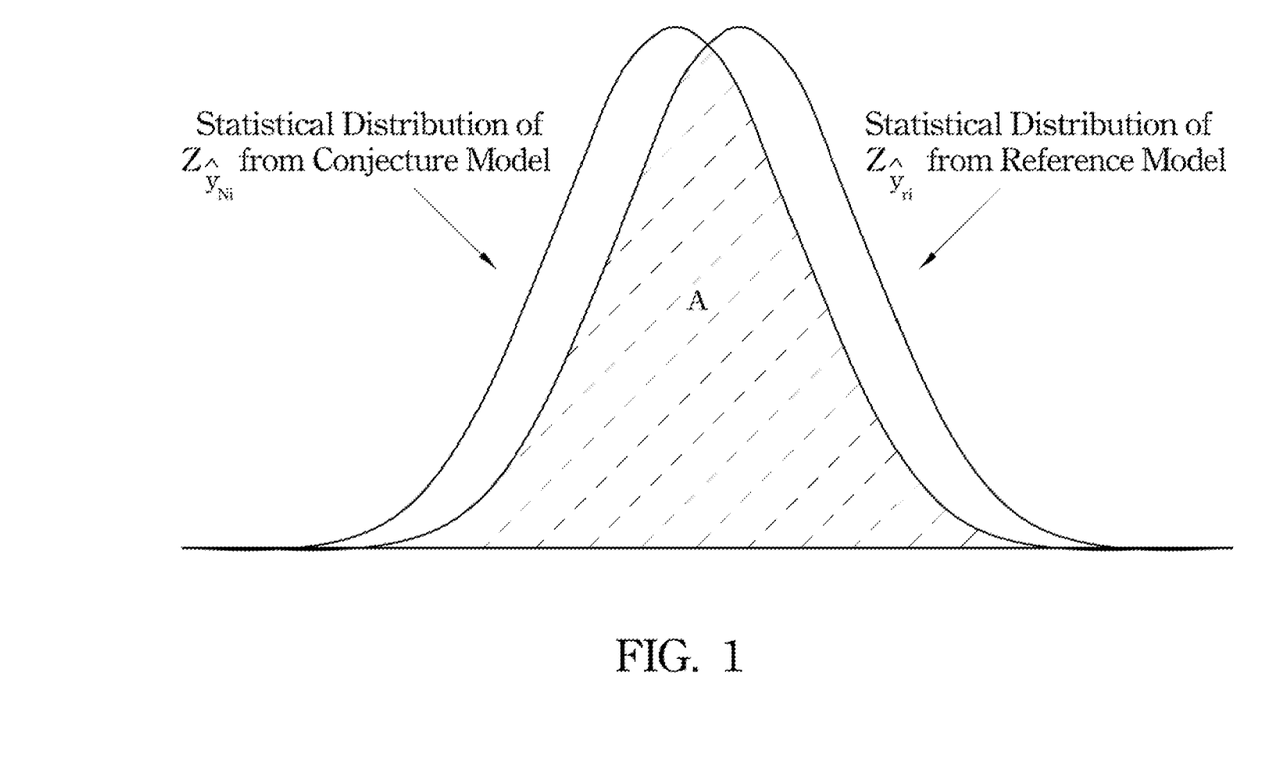
FIG. 1 is a schematic diagram for explaining a reliance index (RI) according to some embodiments of the present invention.

Referring to FIG. 1, FIG. 1 is a schematic diagram for explaining the reliance index (RI) according to the preferred embodiment of the present invention. The RI of the present invention is defined as the intersection-area value (overlap area A) between the statistical distribution $Z_{\hat{y}_{Ni}}$ of the virtual metrology value from the conjecture model (built by such as the NN algorithm) and the statistical distribution $Z_{\hat{y}_r}$ of the reference prediction value from the reference model (built by such as the MR algorithm). As such, the RI equation is listed below:

$$RI = 2 \int_{\frac{Z_{\hat{y}_{Ni}} + Z_{\hat{y}_{ri}}}{2}}^{\infty} \frac{1}{\sqrt{2\pi}\,\sigma} e^{-\frac{1}{2}(\frac{x-\mu}{\sigma})^2} dx \text{ with} \quad (4)$$

$$\mu = Z_{\hat{y}_{Ni}} \text{ if } Z_{\hat{y}_{Ni}} < Z_{\hat{y}_{ri}}$$

$$\mu = Z_{\hat{y}_{ri}} \text{ if } Z_{\hat{y}_{ri}} < Z_{\hat{y}_{Ni}}$$

and $\sigma$ is set to be 1.

The RI increases with increasing overlap area A. This phenomenon indicates that the result obtained using the conjecture model is closer to that obtained from the reference model, and thus the corresponding virtual metrology value is more reliable. Otherwise, the reliability of the corresponding measurement value reduces with decreasing RI. When the distribution $Z_{\hat{y}_{Ni}}$ estimated from: $Z_{\hat{y}_N}$ is fully overlapped with the distribution $Z_{\hat{y}_r}$ estimated from $Z_{\hat{y}_r}$, then according to the distribution theory of statistics, the RI value equals 1; and, when those two distributions are almost separate, the RI value approaches 0.

Hereinafter, the method for calculating the statistical distribution of the virtual metrology values ($Z_{\hat{y}_N}$ and $\hat{\sigma}_{Z_{\hat{y}_N}}$) from the conjecture model is explained.

In the NN conjecture model, if the convergence condition is to minimize SSE, then it can be assumed that "for given $Z_{x_i}$, $Z_{\hat{y}_{Ni}}$ is the distribution with mean $\mu_{Z_{y_i}}$ and standard deviation $\theta_{Z_y}$", namely for given $Z_{x_{i,j}}$, $$Z_{\hat{y}_{Ni}} \sim N(\mu_{Z_{y_i}}, \sigma_{Z_y}^2),$$

where the NN estimating equation of $$\mu_{Z_{y_i}} \text{ is } \hat{\mu}_{Z_{y_i}} = Z_{\hat{y}_{Ni}},$$

and the NN estimating equation of $\sigma_{Z_y}^2$ is $\hat{\sigma}_{Z_y}^2 = \hat{\sigma} Z_{\hat{y}_N}^2$.

Before the NN conjecture model is constructed, the process data must be standardized. The equations for standardizing the process data are presented below:

$$Z_{x_{i,j}} = \frac{x_{i,j} - \bar{x}_j}{\sigma_{x_j}}, i = 1, 2, \ldots, n, n+1, \ldots, m; j = 1, 2, \ldots, p \quad (5)$$

$$\bar{x}_j = \frac{1}{n}(x_{1,j} + x_{2,j} + \ldots + x_{n,j}) \quad (6)$$

$$\sigma_{x_j} = \sqrt{\frac{1}{n-1}[(x_{1,j} - \bar{x}_j)^2 + (x_{2,j} - \bar{x}_j)^2 + \ldots + (x_{n,j} - \bar{x}_j)^2]} \quad (7)$$

wherein
  $x_{i,j}$ is the j-th process parameter in the i-th set of process data,
  $Z_{x_{i,j}}$ is the standardized j-th process parameter in the i-th set of process data;
  $\bar{x}_j$ is the mean of the j-th process data;
  $\sigma_{x_j}$ is the standard deviation of the j-th process data.

The n sets of standardized process data ($Z_{x_{i,j}}$, i=1, 2, . . . , n; j=1, 2, . . . , p) and the n standardized actual measurement values ($Z_{y_i}$, i=1, 2, . . . , n) are utilized to build the NN conjecture model. The m sets of standardized process data ($Z_{x_{i,j}}$, i=1, 2, . . . , m; j=1, 2, . . . , p) are then inputted into the NN conjecture model to obtain the corresponding standardized virtual metrology values:

$$Z_{\hat{y}_{N_1}}, Z_{\hat{y}_{N_2}}, \ldots, Z_{\hat{y}_{N_n}}, Z_{\hat{y}_{N_{n+1}}}, \ldots, Z_{\hat{y}_{N_m}}.$$

Accordingly, the estimated value of $\mu_{Z_{y_i}}$ (i.e.

$$\hat{\mu}_{Z_{y_i}} = Z_{\hat{y}_{N_i}})$$

and the estimated value of $\sigma_{Z_y}$ (i.e. $\hat{\sigma}_{Z_y} = \hat{\sigma} Z_{\hat{y}N}$) can be computed as follows:

$$\hat{\mu}_{Z_{y_i}} = Z_{\hat{y}_{N_i}}, i = 1, 2, \ldots, n, n+1, \ldots, m \quad (8)$$

$$\hat{\sigma}_{Z_{\hat{y}N}} = \sqrt{\frac{1}{n-1}\left[(Z_{\hat{y}_{N_1}} - \overline{Z}_{\hat{y}_N})^2 + (Z_{\hat{y}_{N_2}} - \overline{Z}_{\hat{y}_N})^2 + \ldots + (Z_{\hat{y}_{N_n}} - \overline{Z}_{\hat{y}_N})^2\right]} \quad (9)$$

$$\overline{Z}_{\hat{y}N} = \frac{1}{n}(Z_{\hat{y}_{N_1}} + Z_{\hat{y}_{N_2}} + \ldots + Z_{\hat{y}_{N_n}}) \quad (10)$$

wherein $\overline{Z}_{\hat{y}_N}$ is the mean of the standardized virtual metrology values.

Hereinafter, the method for calculating the reference predication values $$(Z_{\hat{y}_{r_i}} \text{ and } \hat{\sigma}_{Z_{\hat{y}_r}})$$

from the MR model is explained.

The basic assumption of the MR is that "for given $$Z_{x_{i,j}}, Z_{y_{r_i}}$$

is the distribution with mean $\mu_{Z_{y_i}}$ and standard deviation $\sigma_{Z_y}$", namely for given $$Z_{x_{i,j}}, Z_{y_{r_i}} \sim N(\mu_{Z_{y_i}}, \sigma_{Z_y}^2),$$

wherein the MR estimating equation of $\mu_{Z_y}$ is $$\hat{\mu}_{Z_{y_i}} = Z_{\hat{y}_{r_i}},$$

and the MR estimating equation of $\sigma_{Z_y}^2$ is $$\hat{\sigma}_{Z_y}^2 = \hat{\sigma}_{Z_{\hat{y}_r}}^2.$$

To obtain the MR relationship between the n sets of standardized process data $(Z_{x_{i,j}}, i=1, 2, \ldots, n; j=1, 2, \ldots, p)$ and the n standardized actual measurement values, $(Z_{y_i}, i=1, 2, \ldots, n)$, the weighting factors $\beta_r = [\beta_{r0}, \beta_{r1}, \beta_{r2}, \ldots, \beta_{rp}]^T$ corresponding to those p parameters must be defined by using the MR analysis. The relationship between $Z_{y_i}$ and $Z_{x_{i,j}}$ thus is constructed as follows:

$$\beta_{r0} + \beta_{r1} Z_{x_{1,1}} + \beta_{r2} Z_{x_{1,2}} + \ldots + \beta_{rp} Z_{x_{1,p}} = Z_{y_1} \quad (11)$$
$$\beta_{r0} + \beta_{r1} Z_{x_{2,1}} + \beta_{r2} Z_{x_{2,2}} + \ldots + \beta_{rp} Z_{x_{2,p}} = Z_{y_2}$$
$$\ldots$$
$$\beta_{r0} + \beta_{r1} Z_{x_{n,1}} + \beta_{r2} Z_{x_{n,2}} + \ldots + \beta_{rp} Z_{x_{n,p}} = Z_{y_n}$$

Let $$Z_y = \begin{pmatrix} Z_{y_1} \\ Z_{y_2} \\ \vdots \\ Z_{y_n} \end{pmatrix} \quad (12)$$

and $$Z_x = \begin{pmatrix} 1 & Z_{x_{1,1}} & \ldots & Z_{x_{1,p}} \\ 1 & Z_{x_{2,1}} & \ldots & Z_{x_{2,p}} \\ \vdots & \vdots & \ddots & \vdots \\ 1 & Z_{x_{n,1}} & \ldots & Z_{x_{n,p}} \end{pmatrix} \quad (13)$$

The least square method can obtain the estimating equation of $\beta_r$, $\hat{\beta}_r = [\hat{\beta}_{r0}, \hat{\beta}_{r1}, \ldots, \hat{\beta}_{rp}]^T$ as $$\hat{\beta}_r = (Z_x^T Z_x)^{-1} Z_x^T Z_y \quad (14)$$

Therefore, the MR reference model can be obtained as $$Z_{\hat{y}r_i} = \hat{\beta}_{r0} + \hat{\beta}_{r1} Z_{x_{i,1}} + \hat{\beta}_{r2} Z_{x_{i,2}} + \ldots + \hat{\beta}_{rp} Z_{x_{i,p}}, i=1,2,\ldots, n, n+1, \ldots, m \quad (15)$$

Hence, during the conjecture phase, after inputting a set of process data, its MR estimating value $Z_{\hat{y}_{r_i}}$ corresponding thereto can be obtained via equation (15). The MR estimating equation of the standard deviation $\sigma_{Z_y}$ is $\hat{\sigma}_{Z_y}$, with $$\hat{\sigma}_{Z_{\hat{y}_r}} = \sqrt{\frac{1}{n-1}\left[(Z_{\hat{y}_{r_1}} - \overline{Z}_{\hat{y}_r})^2 + (Z_{\hat{y}_{r_2}} - \overline{Z}_{\hat{y}_r})^2 + \ldots + (Z_{\hat{y}_{r_n}} - \overline{Z}_{\hat{y}_r})^2\right]} \quad (16)$$

$$\overline{Z}_{\hat{y}_r} = \frac{1}{n}(Z_{\hat{y}r1} + Z_{\hat{y}r2} + \ldots + Z_{\hat{y}r_n}) \quad (17)$$

After obtaining the NN estimating equations $$(Z_{\hat{y}_{N_i}} \text{ and } \hat{\sigma}_{Z_{\hat{y}_N}})$$

and the MR estimating equations $$(Z_{\hat{y}_{r_i}} \text{ and } \hat{\sigma}_{Z_{\hat{y}_r}}),$$

their normal distribution curves can be depicted, as illustrated in FIG. 1. Thus, the RI of each virtual metrology value can be derived by calculating the intersection area value (overlap area A).

After obtaining the RI, the RI threshold value ($RI_T$) must be defined. If $RI \geq RI_T$, then the reliance level of the virtual metrology value is acceptable. A systematic approach for determining the $RI_T$ is described below.

Before determining the $RI_T$, it is necessary to define a maximal tolerable error limit ($E_L$). The error of the virtual metrology value is an absolute percentage of the difference between the actual measurement value $y_i$ and $\hat{y}_{Ni}$ obtained from the NN conjecture model divided by the mean of all the actual measurement values, $\bar{y}$, namely $$Error_i = \left| \frac{y_i - \hat{y}_{Ni}}{\bar{y}} \right| \times 100\% \qquad (18)$$

Figure 2:
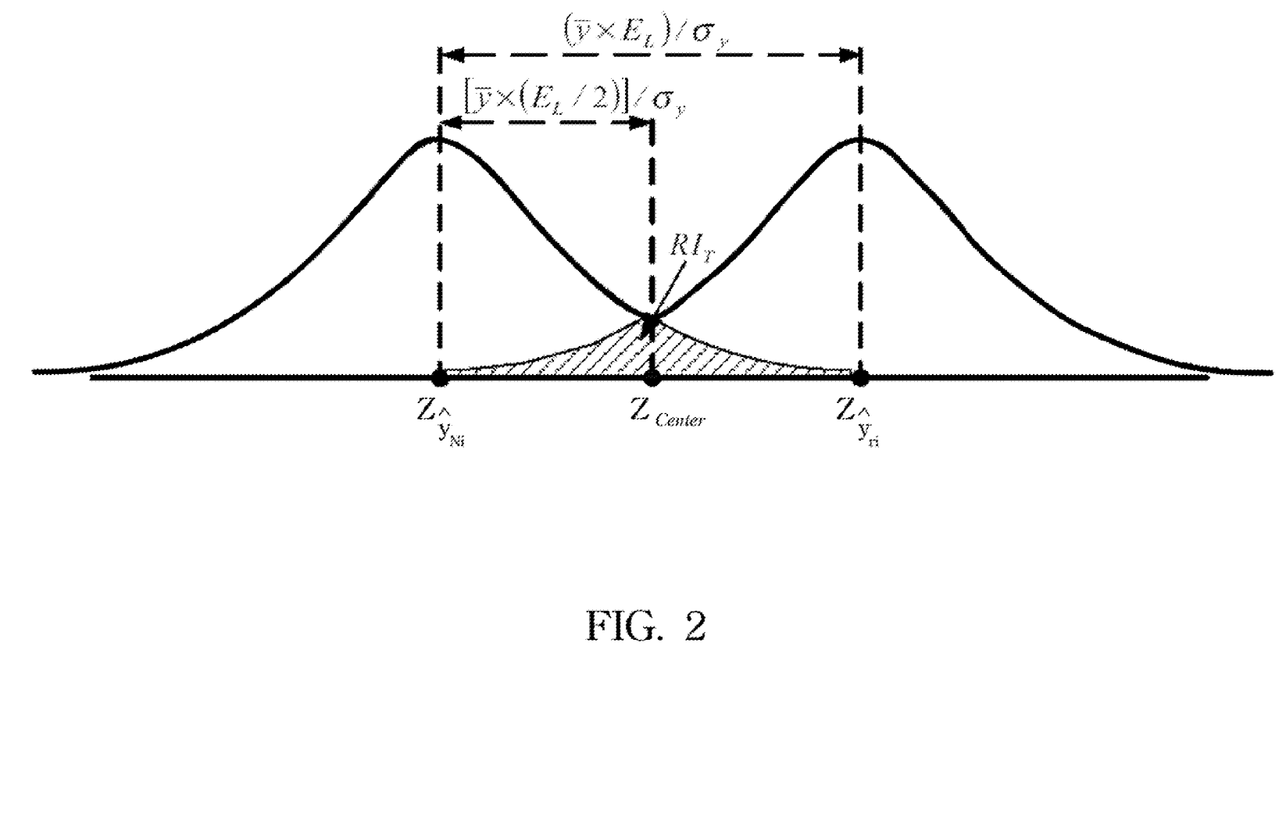
FIG. 2 is a schematic diagram for defining a RI threshold ($RI_T$) according to some embodiments of the present invention.

The $E_L$ can then be specified based on the error defined in equation (18) and the accuracy specification of virtual metrology (VM). Consequently, $RI_T$ is defined as the RI value corresponding to the $E_L$, as shown in FIG. 2. That is $$RI_T = 2 \int_{Z_{Center}}^{\infty} \frac{1}{\sqrt{2\pi}\,\sigma} e^{-\frac{1}{2}\left(\frac{x-\mu}{\sigma}\right)^2} dx \qquad (19)$$

with $\mu$ and $\sigma$ defined in equation (4) and $$Z_{center} = Z_{\hat{y}_{Ni}} + [\bar{y} \times (E_L/2)]/\sigma_y \qquad (20)$$

where $\sigma_y$ is specified in equation (3).

The following explains a method for building a GS model. As mentioned above, when virtual metrology is applied, no actual measurement value is available to verify the accuracy of the virtual metrology value. Therefore, instead of the standardized actual measurement value $Z_{y_i}$, the standardized MR prediction value $Z_{\hat{y}_{rj}}$ is adopted to calculate the RI. This substitution may cause inevitable gauging errors in the RI. To compensate for this unavoidable substitution, a global similarity index (GSI) is provided to help the RI gauge the reliance level of virtual metrology and identifying the key process parameters with large deviations (z score values).

The GSI assesses the degree of similarity between any set of process data and the model set of process data. This model set is derived from all of the sets of historical process data used for building the conjecture model.

The present invention may utilize a statistical distance measure, such as Mahalanobis distance, to quantify the degree of similarity. Mahalanobis distance is a distance measure introduced by P.C. Mahalanobis in 1936. This measure is based on correlation between variables to identify and analyze different patterns of sample sets. Mahalanobis distance is a useful way of determining similarity of an unknown sample set to a known one. This method considers the correlation of the data set and is scale-invariant, namely it is not dependent on the scale of measurements. If the data set has high similarity, the calculated Mahalanobis distance calculated will be relatively small.

The present invention uses the calculated GSI (applying Mahalanobis distance) size to determine whether the newly input set of process data is similar to the model set of process data. If the calculated GSI is small, the newly input set is relatively similar to the model set. Thus the virtual metrology value of the newly input (high-similarity) set is relatively accurate. On the contrary, if the calculated GSI is too large, the newly input set is somewhat different from the model set. Consequently, the virtual metrology value estimated in accordance with the newly input (low-similarity) set has low reliance level in terms of accuracy.

The equations to calculate the standardized process data $Z_{x_{i,j}}$ of the conjecture model are shown in equations (5), (6) and (7). At first, the model set of the process parameters is defined as $X_M = [x_{M,1}, x_{M,2}, \ldots, x_{M,p}]^T$, where $x_{M,j}$ equals $\bar{x}_j$, $j=1, 2, \ldots, p$, so that each element in the model set after standardization (also denoted as the standardized model parameter, $Z_{M,j}$) has a value of 0. Restated, all of the elements in $Z_M = [Z_{M,1}, Z_{M,2}, \ldots, Z_{M,p}]^T$, are 0. Thereafter, the correlation coefficients between the standardized model parameters are calculated.

Assuming that the correlation coefficient between the s-th parameter and the t-th parameter is $r_{st}$ and that there are k sets of data, then $$r_{st} = \frac{1}{k-1} \sum_{l=1}^{k} z_{sl} \cdot z_{tl} = \frac{1}{k-1} (z_{s1} \cdot z_{t1} + z_{s2} \cdot z_{t2} + \ldots + z_{sk} \cdot z_{tk}) \qquad (21)$$

After calculating the correlation coefficients between the standardized model parameters, the matrix of correlation coefficients can be obtained as $$R = \begin{bmatrix} 1 & r_{12} & \ldots & r_{1p} \\ r_{21} & 1 & \ldots & r_{2p} \\ \vdots & \vdots & \ddots & \vdots \\ r_{p1} & r_{p2} & \ldots & 1 \end{bmatrix} \qquad (22)$$

Assuming that the inverse matrix ($R^{-1}$) of R is defined as A, then $$A = R^{-1} = \begin{bmatrix} a_{11} & a_{12} & \ldots & a_{1p} \\ a_{21} & a_{22} & \ldots & a_{2p} \\ \ldots & \ldots & \ldots & \ldots \\ a_{p1} & a_{p2} & \ldots & a_{pp} \end{bmatrix} \qquad (23)$$

Hence, the equation for calculating the Mahalanobis distance ($D_\lambda^2$) between the standardized $\lambda$-th set process data ($Z_\lambda$) and the standardized model set process data ($Z_M$) is as follows.

$$D_\lambda^2 = (Z_\lambda - Z_M)^T R^{-1} (Z_\lambda - Z_M) \qquad (24)$$
$$= Z_\lambda^T R^{-1} Z_\lambda$$

Finally, equation (25) is obtained.

$$D_\lambda^2 = \sum_{j=1}^{p} \sum_{i=1}^{p} a_{ij} z_{i\lambda} z_{j\lambda} \qquad (25)$$

The GSI of the standardized $\lambda$-th set process data is, then, equal to $D_\lambda^2/p$.

After obtaining the GSI, the GSI threshold ($GSI_T$) should be defined as the following:

$$GSI_T = a * \overline{GSI}_{LOO} \qquad (26)$$

In the so-called cross validation's leave-one-out (LOO) method, one sample data set is selected from all sets of process data used for building models as a simulated on-line test sample set, and then the remaining sets of process data are utilized to construct a GS model, and thereafter the GSI model is used to compute a GSI value for the test sample set, i.e. $GSI_{LOO}$. The above steps are repeated on all of the sample data sets (process data) used for building models, thus computing all of the $GSI_{LOO}$ values of the respective sample data sets. Therefore, $\overline{GSI}_{LOO}$ shown in equation (26)

stands for, for example, the 90% trimmed mean of all the $GSI_{LOO}$ values computed by the sample data sets respectively. The "a" shown in equation (26) is between 2 and 3, and can be slightly adjusted in accordance with the actual conditions, wherein "a" is predetermined to be 3.

A method for constructing a $DQI_X$ model is described as follows. Assume that n sets of historical process data are received for constructing the first $DQI_X$ model, wherein each set of historical process data is composed of p parameters. These n sets of historical process data are applied to generate p eigenvectors with p corresponding eigenvalues ($\lambda_1 \geq \lambda_2 \geq \ldots \geq \lambda_p$) in descending order by the principal component analysis (PCA). Then, a set of k significant eigenvalues (with $\lambda \geq 1$) is selected for constructing a feature-extraction matrix M, which is expressed as:

$$M = \begin{bmatrix} [\text{eigenvector 1}] \\ [\text{eigenvector 2}] \\ \vdots \\ [\text{eigenvector k}] \end{bmatrix}_{k*p} \quad (27)$$

The method for computing the $DQI_X$ value is explained as follows.

At first, equation (28) is applied to transform the $i^{th}$ input set of process data $X_i$ to k data feature variables $A_i[a_1, a_2, \ldots, a_k]$.

$$A_i = M \cdot X_i \quad (28)$$

Then, these k data feature variables are transformed to $Z_A = [Z_{a_1}, Z_{a_2}, \ldots, Z_{a_k}]$, which is then converted by the Euclidean distance (ED) algorithm into a consolidated index, i.e. $DQI_X$ value:

$$DQI_{X_i} = \sqrt{\sum_{j=1}^{k} (z_{a_i,j} - \bar{z}_{a_j}) * (z_{a_i,j} - \bar{z}_{a_j})^T} \quad (29)$$

where i represents the $i^{th}$ input set of process data;
$\bar{Z}_{a_j}$: the mean of the j-th standardized variable of the training samples.

Theoretically, the value of $\bar{Z}_{a_j}$ is zero, and therefore Equation (29) can be simplified as:

$$DQI_{X_i} = \sqrt{\sum_{j=1}^{k} (z_{a_i,j}) * (z_{a_i,j})^T} \quad (30)$$

Meanwhile, the cross validation's leave-one-out (LOO) method is used to determine process data quality threshold ($DQI_{X_T}$) as:

$$DQI_{X_T} = a * \overline{DQI_{X_{LOO}}} \quad (31)$$

In the so-called cross validation's leave-one-out (LOO) method, one sample data set is selected from all sets of process data used for building models as a simulated on-line test sample set, and then the remaining sets of historical process data are utilized to construct a $DQI_X$ model, and thereafter the $DQI_X$ model newly built is used to compute a $DQI_X$ value for the simulated on-line test sample set, i.e. $DQI_{X_{LOO}}$. The above steps are repeated on all of the sample data sets (process data) used for building models, thus computing all of the $DQI_{X_{LOO}}$ values of the respective sample data sets. Therefore, $\overline{DQI_{X_{LOO}}}$ shown in equation (31) stands for, for example, the 90% trimmed mean of all the $DQI_{X_{LOO}}$ values computed by the sample data sets respectively. The "a" shown in equation (31) is between 2 and 3, and can be slightly adjusted in accordance with the actual conditions, wherein "a" is predetermined to be 3.

It is noted that the feature-extraction matrix M and the $DQI_X$ compose a $DQI_X$ model, and the $DQI_X$ model will be updated (in the model-refreshing procedure) in accordance with a condition for retraining or tuning.

Thereafter, Z-score values of the historical process data are computed. Then, a $DQI_y$ model is created, in which the $DQI_y$ model is composed of m similar patterns In the present embodiment, the m similar patterns $\{P_1, P_2, \ldots, P_m\}$ are sorted from Z-score values of those n sets of historical process data by applying adaptive resonance theory 2 (ART2) with $\rho = 0.98$.

The method for computing the $DQI_y$ values is described as follows. At first, when a new actual measurement value $y_i$ is collected, the Z-score value $Z_{X_{Gj}}$ corresponding to the actual measurement value v are applied by the adaptive resonance theory 2 (ART2) to search for the most similar pattern $P_q = [X_{q,1}, X_{q,2}, \ldots, X_{q,v}]$ from the similar patterns $\{P_1, P_2, \ldots, P_m\}$. Then, the v samples ($v \geq 2$) inside the $P_q = [X_{q,1}, X_{q,2}, \ldots, X_{q,v}]$ with their corresponding actual measurement values, $Y_q = [y_{q,1}, y_{q,2}, \ldots, y_{q,v}]$, and this new actual measurement value $y_j$ are utilized to compute the $DQI_{y_j}$ and the threshold value ($DQI_{y_T}$) of the $DQI_y$. The $DQI_{y_j}$ of $y_j$ is obtained as normalized variability (NV):

$$DQI_{y_j} = \frac{|y_j - \bar{y}_q|}{\bar{y}_q} \quad (32)$$

$$\text{where } \bar{y}_q = \frac{1}{v} \sum_{l=1}^{v} y_{q,l} \quad (33)$$

where $\bar{y}_q$: the mean of all $y_{q,1}$ in $Y_q$;
v: the number of samples inside the pattern $P_q$.

The $DQI_{y_t}$ of a certain pattern $P_q$ is defined to be the maximal-tolerable variance of the $P_q$. Suppose that $y_i$ is the maximal-tolerable metrology value that possesses the maximal-tolerable variance in $P_q$, then $y_i$ can be presented as:

$$y_i = \bar{y}_q + R_{max} \text{ or } y_i = \bar{y}_q - R_{max} \quad (34)$$

where $R_{max}$ is the maximal-tolerable variance;

$$R_{max} = \max(R_{P_1}, R_{P_2}, \ldots, R_{P_m}) \quad (35)$$

where $R_{P_i}$, $i = 1, 2, \ldots, m$, is the range in pattern $P_i$, and m is the total number of all the similar-pattern groups.

By adding $y_i$ into the similar pattern $P_q$, the $DQI_{y_t}$ can be acquired as:

$$DQI_{y_T} = \frac{|y_t - \bar{y}_q|}{\bar{y}_q} \quad (36)$$

After obtaining the $DQI_{y_j}$ and $DQI_{y_t}$, if $DQI_{y_j} > DQI_{y_t}$ is true, then it means that the new actual measurement value is abnormal; otherwise, the new actual measurement value is normal.

The aforementioned PCA, LOO, ART2, Z-score and ED algorithms all are known to one having ordinary skill in the art, and thus the details thereof are not described herein.

Figure 3:
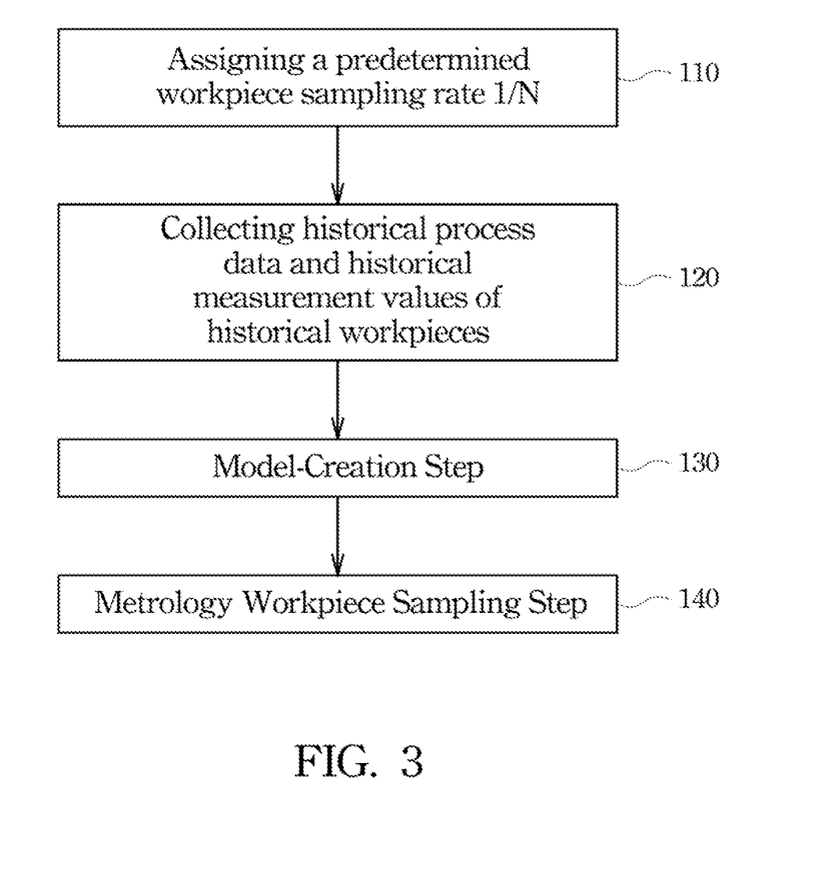
FIG. 3 is a schematic flow chart showing a metrology sampling method according various embodiments of the present invention.

Referring to FIG. 3, FIG. 3 is a schematic flow chart showing a metrology sampling method according various embodiments of the present invention. At first, a predetermined workpiece sampling rate 1/N is assigned (step 110), in which the predetermined workpiece sampling rate is directed to selecting the $N^{th}$ workpiece in each N workpieces processed by a process tool as a workpiece expected to be measured. For example, a conventional workpiece sampling rate workpiece is defined as selecting the $25^{th}$ workpiece in each 25 workpieces (workpiece count=25) as a workpiece expected to be measured after the each 25 workpieces are processed by the process tool. Embodiments of the present invention adopts a variable "workpiece count" to enable the application of the predetermined workpiece sampling rate of which the initial value is 0. Theoretically, the workpiece with the workpiece count equal to N will be selected as the workpiece expected to be measured. Thereafter, a plurality of sets of historical process data used by the process tool for processing a plurality of historical workpieces are collected, and a plurality of historical measurement values of the historical workpieces corresponding to the sets of historical process data are collected (step 120). Then, a model-creation step 130 is performed to build a RI model (a conjecture model and a reference model), a $DQI_X$ model, a $DQI_y$ model and a GSI model, and to compute a $DQI_X$ threshold, a $DQI_y$ threshold and a GSI threshold. The details of the model-creation step 130 are explained in the above. After the model-creation step 130 is completed, a metrology workpiece sampling step 140 can then be performed. Hereinafter, the five scenarios considered by the ISD scheme of the metrology workpiece sampling step 140 are explained.

Scenario 1: a stable process is considered. When no status-changes of a process tool occur and all of the RI, GSI, $DQI_X$, and $DQI_y$ values of a workpiece processed by the process tool are within their respective thresholds in a manufacturing process, i.e. $RI \geq RI_T$; $GSI \leq GSI_T$; $DQI_X \leq DQI_{X_T}$; $DQI_y \leq DQI_{y_T}$, then this process is stable. At this situation, no actual measurement value is needed to update the VM model, and thus the ISD scheme can set N to a greater number (i.e. a lower predetermined workpiece sampling rate) without affecting the accuracy of VM models.

Scenario 2: the status of the process tool is changed. A possible status change of the process tool may occur when tool maintenance, repair, or recipe adjustment is performed. At this situation, embodiments of the present invention will request an actual measurement for the workpiece which is being processed when the status of the process tool is changed, and reset the workpiece count to 0. For example, if the workpiece originally expected to be measured is the $25^{th}$ workpiece, and the status of the process tool is changed when the second workpiece is being processed, embodiments of the present invention performs actual metrology on the second workpiece, and the next workpiece expected to be measured is the $27^{th}$ workpiece.

Scenario 3: the $DQI_X$ value of the workpiece is abnormal (i.e. $DQI_X > DQI_{X_T}$). The function of the $DQI_X$ value is to check the quality of the set of process data used by the process tool for processing the workpiece. To prevent abnormal process data from deteriorating the VM models, the workpiece with abnormal $DQI_X$ value should not be selected for measurement. In other words, the measurement for the workpiece with abnormal $DQI_X$ value will be skipped. If the workpiece with abnormal $DQI_X$ value is originally expected (scheduled) to be measured (at this moment, the workpiece count for controlling workpiece sampling is N), embodiments of the present invention does not perform actual metrology on the workpiece, but instead, request an actual measurement on a next workpiece. If the $DQI_X$ value of this next workpiece is normal (at this moment, the workpiece count for controlling workpiece sampling is greater than N), actual metrology is performed on this next workpiece. If the $DQI_X$ value of this next workpiece is still abnormal, the measurement of this next workpiece is skipped. Thereafter, the same operations are used to consider another next workpiece sequentially.

Scenario 4: the GSI value or the RI value of the workpiece is abnormal ($GSI > GSI_T$ or $RI < RI_T$). The purpose of the RI value is to gauge the reliance level of a VM value. If the RI value of the workpiece is abnormal ($RI < RI_T$), it represents that the degree of reliability of the VM value of the workpiece is poor, and the actual measurement value of the workpiece is needed to retune or retrain the VM models. The purpose of the GSI value is to evaluate deviations of process data. A process-data deviation of the workpiece may result in a deviation of its corresponding actual measurement value. As such, the workpiece with the abnormal GSI value needs to be inspected. However, if the abnormal RI value or GSI value just happens once, then this may be a false alarm caused by noise or other factors. To confirm that a real deviation is detected, when at least a certain number of consecutive workpieces (such as two or four) have abnormal RI or GSI values, embodiments of the present invention then perform actual metrology on the second or fourth workpiece.

Scenario 5: the $DQI_y$ value of the workpiece is abnormal (i.e. $DQI_y > DQI_{y_T}$). The function of the $DQI_y$ value is to evaluate the quality of the actual measurement value of the workpiece. If the quality of the actual measurement value of the workpiece is not good, the actual measurement value of the workpiece cannot be used for retuning or retraining the VM models. Instead, embodiments of the present invention request an actual measurement on a next workpiece promptly.

Figure 4:
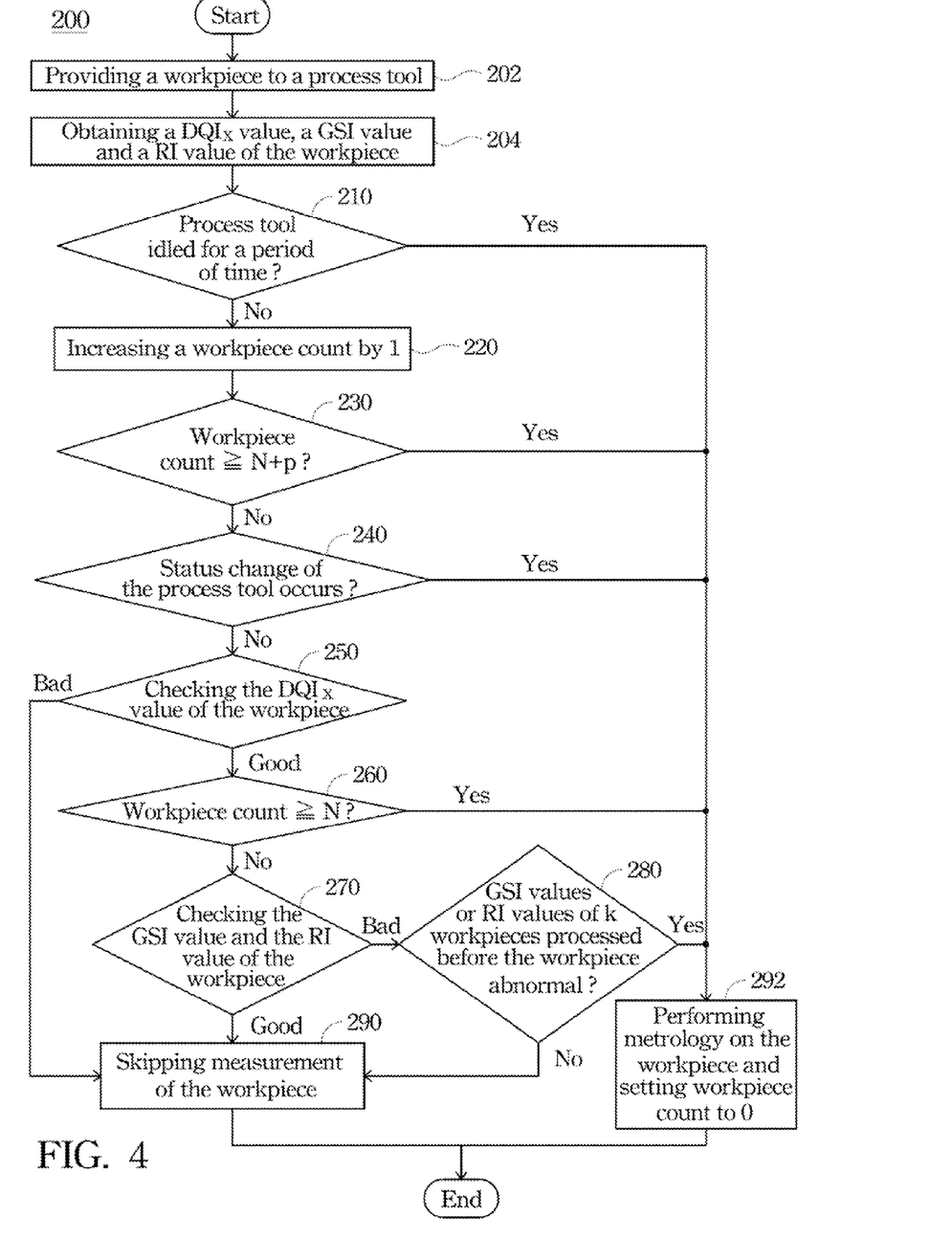
FIG. 4 is a schematic flow chart showing a metrology workpiece sampling step according various embodiments of the present invention.

Hereinafter, a flow process of the metrology workpiece sampling step 140 is explained, wherein the metrology workpiece sampling step 140 includes a sampling step 200 shown in FIG. 4 and step 201 shown in FIG. 5.

In the sampling step 200, at first, a workpiece is provided to a process tool (step 202), in which the process tool has a set of process data used to process the workpiece. The set of process data of the workpiece is inputted into the $DQI_X$ model and the GSI model built in the model-creation step 130, thereby obtaining a $DQI_X$ value, a GSI value and a RI value of the workpiece (step 204). In step 204, the set of process data of the workpiece is also inputted into the conjecture model built in the model-creation step 130, thereby computing a virtual metrology (VM) value of the workpiece; and the set of process data of the workpiece is also inputted into the reference model built in the model-creation step 130, thereby computing a reference prediction value of the workpiece. Thereafter, an overlap area between the statistical distribution of the virtual metrology value of the workpiece and the statistical distribution of the reference prediction value of the workpiece is calculated to generate a RI value of the workpiece, in which the RI increases with increasing overlap area, representing that the corresponding virtual metrology value is more reliable.

Thereafter, step 210 is performed to check if the process tool has been idled for a period of time (for example, idled for more than one day). When the checking result of step 210 is true ("yes"), the workpiece is regarded as the first workpiece after the idle period and step 292 has to be performed to perform metrology on the workpiece by using a metrology tool and set a workpiece count to 0, thereby confirming if the process tool is normal. When the checking result of step 210 is false ("no"), the workpiece count is increased by 1 (step 220). Then, step 230 is performed to check if the workpiece count is greater than or equal to N+p, where p is a positive integer (such as 5), and N is used to define the predetermined workpiece sampling rate 1/N. For preventing too many workpieces from skipping measurement, a safety threshold is set in step 230 to force a workpiece measurement to be performed after a certain amount of workpieces are skipped from measurement. Certainly, step 230 is optional, and embodiments of the present invention may omit this step. When the checking result of step 230 is true ("yes"), the metrology tool is used to perform metrology on the workpiece and the workpiece count is set to 0 (step 292). When the checking result of step 230 is false ("no"), step 240 is performed to check if a status change of the process tool occurs (for example, when tool maintenance, repair, or recipe adjustment etc. is performed.). When the checking result of step 240 is true ("yes"), the metrology tool is used to perform metrology on the workpiece by and the workpiece count is set to 0 (step 292), thereby confirming if the process tool is normal.

When the checking result of step 240 is false ("no"), step 250 is performed to check if the $DQI_X$ value of the workpiece is good or bad. When the $DQI_X$ value is greater than the $DQI_X$ threshold, it represents that the quality of the set of process data of the workpiece (the $DQI_X$ value) is not good (the checking result of step 250 is "bad"). Because the actual measurement value of the workpiece produced by using the set of process data with the abnormal $DQI_X$ value is not reliable, the measurement of the workpiece is skipped (step 290). When the $DQI_X$ value is smaller than or equal to the $DQI_X$ threshold, it represents that the quality of the set of process data of the workpiece is good (the checking result of step 250 is "good"), and step 260 is performed to check if the workpiece count is greater than or equal to N. When the checking result of step 260 is true ("yes"), it represents that the workpiece is the workpiece expected (scheduled) to be measured, metrology should be performed on the workpiece and the workpiece count is set to 0 (step 292).

When the checking result of step 260 is false ("no"), step 270 is performed to check if the GSI value and the RI value of the workpiece are good or bad. When the GSI value of the workpiece is smaller than or equal to the GSI threshold and the RI value of the workpiece is greater than or equal to the RI threshold, it represents that the virtual metrology value conjectured by using the set of process data of the workpiece is reliable (the checking result of step 270 is "good"), and thus the workpiece does not need to be measured (step 290). When the GSI value of the workpiece is greater than the GSI threshold or the RI value of the workpiece is smaller than the RI threshold, it represents that the virtual metrology value conjectured by using the set of process data of the workpiece is not reliable (the checking result of step 270 is "bad"), the workpiece may need to be measured. However, if the abnormal RI value or GSI just happens once, it may be a false alarm caused by noise or other factors, and thus, when at least a certain number of consecutive workpieces (such as two or four) have abnormal RI or GSI values, embodiments of the present invention then perform: actual metrology on the second or fourth workpiece. In other words, when the checking result of step 270 is "bad", step 280 is performed to check if the GSI values of k workpieces (such as the previous one or three workpieces) processed before the workpiece all are greater than the GSI threshold or the RI values of k workpieces processed before the workpiece all are smaller than the RI threshold, where k is a positive integer. When the checking result of the step 280 is true ("yes"), the metrology tool is used to perform metrology on the workpiece and the workpiece count is set to 0 (step 292). When the checking result of the step 280 is false ("no"), the measurement of the workpiece is skipped (step 290). It is worthy to be noted that step 270 also may only check if the GSI value of the workpiece is good or bad. If the GSI value of the workpiece is too large, it represents that the set of process data of the workpiece have some differences from the sets of process data used for model building, such that the quality of the workpiece is likely to be abnormal, and needs actual metrology. It can be known from the above, with the applications of the embodiments of the present invention, a user may wait until the process tool has processed more workpieces to select a workpiece for measurement, i.e. N can be increased to lower the predetermined workpiece sampling rate 1/N without worrying to skip the measurement of the abnormal workpiece that ought to be measured. Thus, the embodiments of the present invention can effectively lower the predetermined workpiece sampling rate. However, the predetermined workpiece sampling rate also can be effectively lowered by only performing step 250 (checking the $DQI_X$ value of the workpiece), step 260 (checking if the workpiece is the workpiece expected to be measured) and step 270 (checking the GSI value and the RI value of the workpiece, or only checking the GSI value of the workpiece).

Figure 5:
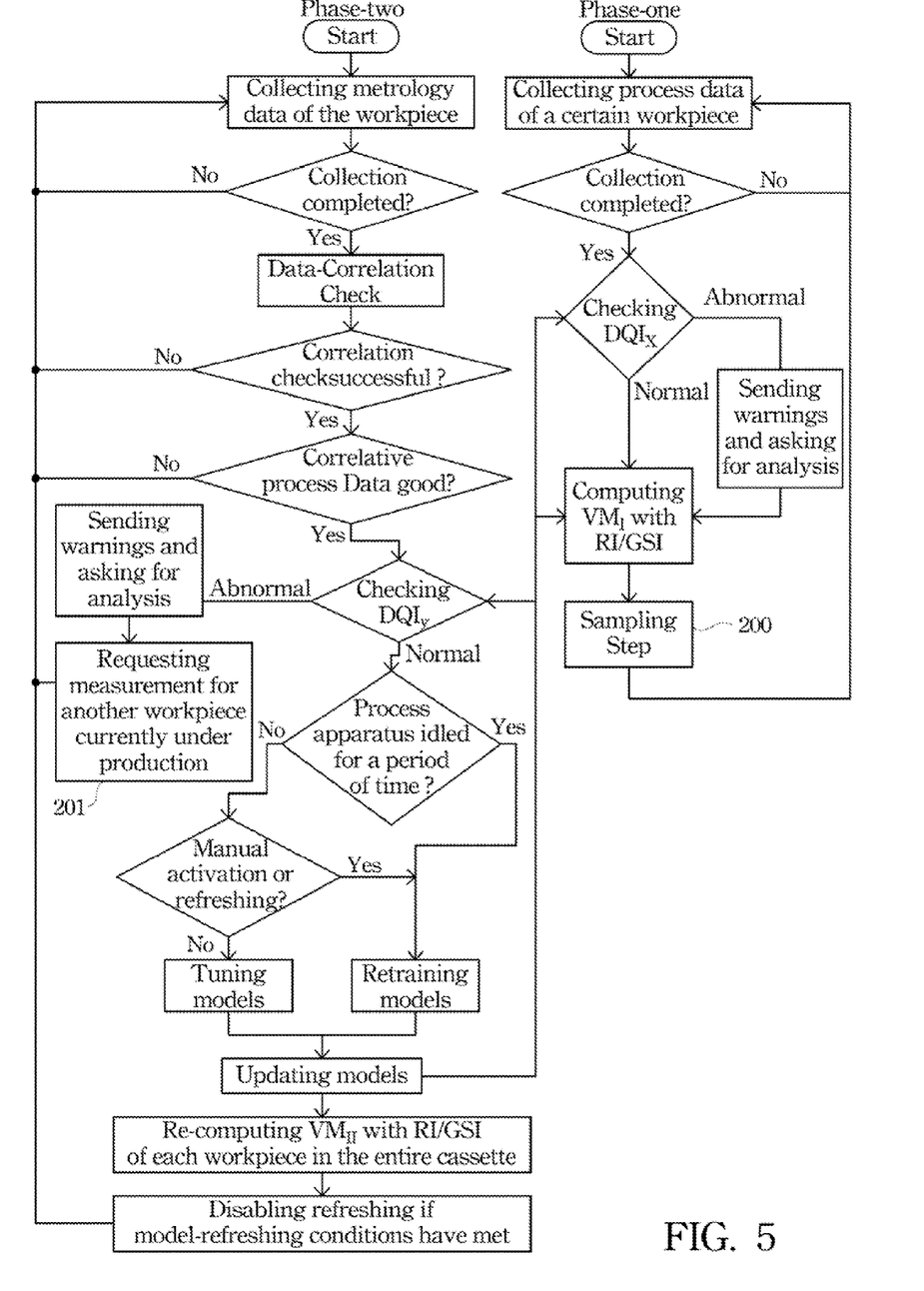
FIG. 5 is a schematic flow chart showing a virtual metrology method according various embodiments of the present invention.

Besides, after the actual metrology is performed on the workpiece, metrology, the workpiece sampling step 140 is also directed to evaluation of a $DQI_y$ value of a workpiece, as shown in step 201 of FIG. 5. At first, an actual measurement value of the workpiece and a set of process data corresponding to the actual measurement value are collected. The set of process data is converted to a set of z scores. The set of z scores and the actual measurement value are inputted into the $DQI_y$ model, thereby computing a $DQI_y$ value of the actual measurement value of the workpiece. When the $DQI_y$ value of the workpiece is greater than the $DQI_y$ threshold, it represents that the actual measurement value is abnormal and cannot be used for tuning or changing models. For making up such insufficiency, another workpiece which is currently under production has to be requested for measurement (i.e. the workpiece count is set to N).

It is understood that the metrology sampling method of the present invention are performed by the aforementioned steps. A computer program of the present invention stored on a non-transitory tangible computer readable recording medium is used to perform the metrology sampling method described above. The aforementioned embodiments can be provided as a computer program product, which may include a machine-readable medium on which instructions are stored for programming a computer (or other electronic devices) to perform a process based on the embodiments of the present invention. The machine-readable medium can be, but is not limited to, a floppy diskette, an optical disk, a compact disk-read-only memory (CD-ROM), a magneto-optical disk, a read-only memory (ROM), a random access memory (RAM), an erasable programmable read-only memory (EPROM), an electrically erasable programmable read-only memory (EEPROM), a magnetic or optical card, a flash memory, or another type of media/machine-readable medium suitable for storing electronic instructions. Moreover, the embodiments of the present invention also can be downloaded as a computer program product, which may be transferred from a remote computer to a requesting computer by using data signals via a communication link (such as a network connection or the like).

On the other hand, a metrology sampling method according to the embodiments of the present invention also can be combined with a method for automatic virtual metrology (AVM) disclosed by U.S. Pat. No. 8,095,484 B2. Referring to FIG. 5, FIG. 5 is a schematic flow chart showing a virtual metrology method according various embodiments of the present invention. After all of the steps in a phase-one virtual metrology are completed, the sampling step 200 is performed to determine if a workpiece needs actual measurement. In a phase-two virtual metrology, when an actual measurement value of a certain workpiece is obtained, the $DQI_y$ value of the workpiece is checked. When the $DQI_y$ value of the workpiece is greater than the $DQI_y$ threshold, step 201 is performed to request measurement for another workpiece which is currently under production (i.e. set the workpiece count to N). After the metrology sampling method according to the embodiments of the present invention are combined with the virtual metrology method, an actual measurement value of a workpiece can be obtained in time for tuning or retraining the VM models, thereby assuring the VM accuracy.

It can be known from the aforementioned embodiments that, by using the ISD scheme constructed by various index values representing status changes or abnormal information of a process tool during a production process, the present invention can effectively assure the VM accuracy and greatly lower the workpiece sampling rate.

It will be apparent to those skilled in the art that various modifications and variations can be made to the structure of the present invention without departing from the scope or spirit of the invention, in view of the foregoing, it is intended that the present invention cover modifications and variations of this invention provided they fall within the scope of the following claims.

What is claimed is:

1. A metrology sampling method, comprising:
    collecting a plurality of sets of historical process data used by a process tool for processing a plurality of historical workpieces;
    performing a model-creation step, comprising:
        building a $DQI_X$ (Process Data Quality Index) model and a GSI (Global Similarity Index) model and computing a $DQI_X$ threshold and a GSI threshold by using the sets of historical process data; and
    performing a metrology workpiece sampling step, comprising:
        providing a workpiece, a next workpiece and/or another next workpiece to the process tool, the process tool having a set of process data for processing the workpiece, a set of process data for processing the next workpiece, and/or a set of process data for processing the another next workpiece;
        inputting the set of process data of the workpiece, the set of process data for processing the next workpiece, and/or the set of process data for processing the another next workpiece into the $DQI_X$ model and the GSI model, thereby obtaining a $DQI_X$ value and a GSI value of the set of process data of the workpiece, a $DQI_X$ value of the set of process data of the next workpiece and/or a $DQI_X$ value of the set of process data of the another next workpiece;
        skipping a measurement of the workpiece performed by a metrology tool when the $DQI_X$ value of the set of process data of the workpiece is greater than the $DQI_X$ threshold;
        checking if the workpiece is a workpiece expected to be measured when the $DQI_X$ value of the set of process data of the workpiece is greater than the $DQI_X$ threshold, thereby obtaining a first determination result;
        performing metrology on a next workpiece by using the metrology tool when the first determination result is true and the $DQI_X$ value of the set of process data of the next workpiece is smaller than or equal to the $DQI_X$ threshold;
        performing metrology on another next workpiece by using the metrology tool when the first determination result is true and the $DQI_X$ value of the set of process data of the next workpiece is greater than the $DQI_X$ threshold and the $DQI_X$ value of the set of process data of the another next workpiece is smaller than or equal to the $DQI_X$ threshold;
        checking if the workpiece is the workpiece expected to be measured when the $DQI_X$ value of the set of process data of the workpiece is smaller than or equal to the $DQI_X$ threshold, thereby obtaining a first checking result;
        performing metrology on the workpiece by using the metrology tool when the first checking result is true, thereby obtaining an actual measurement value of the workpiece;
        checking if the GSI value of the set of process data of the workpiece is smaller than or equal to the GSI threshold when the first checking result is false, thereby obtaining a second checking result; and
        skipping the measurement of the workpiece performed by the metrology tool when the second checking result is true.

2. The metrology sampling method of claim 1, further comprising:
    collecting a plurality of historical measurement values of the historical workpieces corresponding to the sets of historical process data;
    performing the model-creation step, further comprising:
        building a conjecture model in accordance with a conjecture algorithm by using the sets of historical process data and the historical measurement values;
        building a reference model in accordance with a reference prediction algorithm by using the sets of historical process data and the historical measurement values, wherein the conjecture algorithm is different from the reference prediction algorithm; and
        computing a RI (Reliance Index) threshold based on a maximal tolerable error limit defined by errors of virtual metrology values obtained from the conjecture mode;
        inputting the set of process data into the conjecture model, thereby computing a virtual metrology value of the workpiece;
        inputting the set of process data into the reference model, thereby computing a reference prediction value of the workpiece;
        calculating an overlap area between the statistical distribution of the virtual metrology value of the workpiece and the statistical distribution of the reference prediction value of the workpiece, thereby generating a RI value of the workpiece;
        checking if the RI value of the workpiece is greater than or equal to the RI threshold, thereby obtaining a third checking result; and skipping the measurement of the workpiece performed by the metrology tool when the third checking result is true.

3. The metrology sampling method of claim 2, further comprising:
performing metrology on the workpiece by using the metrology tool when the second checking result or the third checking result is false, and the GSI values of k workpieces processed before the workpiece all are greater than the GSI threshold or the RI values of k workpieces processed before the workpiece all are smaller than the RI threshold, thereby obtaining the actual measurement value of the workpiece, wherein k is a positive integer.

4. The metrology sampling method of claim 2, wherein the conjecture algorithm and the reference prediction algorithm are respectively a back propagation neural network (BPNN) algorithm, a general regression neural network (GRNN) algorithm, a radial basis function neural network (RBFNN) algorithm, a simple recurrent network (SRN) algorithm, a support vector data description (SVDD) algorithm, a support vector machine (SVM) algorithm, a multiple regression (MR) algorithm, a partial least squares (PLS) algorithm, a nonlinear iterative partial least squares (NIPALS) algorithm or generalized linear models (GLMs).

5. The metrology sampling method of claim 2, wherein the model-creation step further comprises:
building a $DQI_y$ (Metrology Data Quality Index) model by using the historical measurement values and the sets of historical process data in accordance with normalized variability (NV) and a clustering algorithm, wherein the clustering algorithm is an adaptive resonance theory 2 (ART2), a fuzzy adaptive resonance theory (Fuzzy ART) or a k-means clustering algorithm; and
computing a $DQI_y$ threshold by applying the sets of historical process data and historical measurement values to the $DQI_y$ model in accordance with the concept of maximal-tolerable variance of similar patterns;
the metrology workpiece sampling step further comprising:
collecting the actual measurement value of the workpiece and the set of process data corresponding to the actual measurement value;
converting the set of process data used for producing the workpiece to a set of z scores;
inputting the set of z scores and the actual measurement value into the $DQI_y$ model, thereby computing a $DQI_y$ value of the actual measurement value of the workpiece; and
requesting measurement for another workpiece which is currently under production by using the metrology tool when the $DQI_y$ value of the workpiece is greater than the $DQI_y$ threshold.

6. The metrology sampling method of claim 1, wherein the GSI model is built in accordance with a Mahalanobis distance algorithm, an Euclidean Distance algorithm, or a centroid method, and the $DQI_X$ model is built in accordance with a principal component analysis (PCA) and an Euclidean distance algorithm, the model-creation step further comprising:
computing the GSI threshold by applying the sets of historical process data in accordance with a cross validation's leave-one-out (LOO) method to; and
computing the $DQI_X$ threshold by using the historical process data and by applying the cross validation's leave-one-out (LOO) method to the $DQI_X$ model.

7. A metrology sampling method, comprising:
assigning a predetermined workpiece sampling rate 1/N, wherein the predetermined workpiece sampling rate is directed to selecting the $N^{th}$ workpiece in each N workpieces processed by a process tool as a workpiece expected to be measured;
collecting a plurality of sets of historical process data of a plurality of historical workpieces;
performing a model-creation step, comprising:
building a $DQI_X$ model and a GSI model and computing a $DQI_X$ threshold and a GSI threshold by using the sets of historical process data;
performing a metrology workpiece sampling step, comprising:
providing a workpiece, a next workpiece and/or another next workpiece to the process tool, the process tool having a set of process data for processing the workpiece, a set of process data for processing the next workpiece, and/or a set of process data for processing the another next workpiece;
inputting the set of process data of the workpiece, the set of process data for processing the next workpiece, and/or the set of process data for processing the another next workpiece into the $DQI_X$ model and the GSI model, thereby obtaining a $DQI_X$ value and a GSI value of the set of process data of the workpiece, a $DQI_X$ value of the set of process data of the next workpiece, and/or a $DQI_X$ value of the set of process data of the another next workpiece;
increasing a workpiece count by 1;
performing a first checking step to check if the $DQI_X$ value of the set of process data of the workpiece is smaller than or equal to the $DQI_X$ threshold, thereby obtaining a first checking result;
skipping a measurement of the workpiece performed by a metrology tool when the first checking result is false;
checking if the workpiece is the workpiece expected to be measured when the first checking result is false, thereby obtaining a first determination result;
performing metrology on the next workpiece by using the metrology tool when the first determination result is true and the $DQI_X$ value of the set of process data of the next workpiece is smaller than or equal to the $DQI_X$ threshold;
performing metrology on the another next workpiece by using the metrology tool when the first determination result is true and the $DQI_X$ value of the set of process data of the next workpiece is greater than the $DQI_X$ threshold and the $DQI_X$ value of the set of process data of the another next workpiece is smaller than or equal to the $DQI_X$ threshold;
performing a second checking step to check if the workpiece count is greater than or equal to N when the first checking result is true, thereby obtaining a second checking result;
performing metrology on the workpiece by using the metrology tool and setting the workpiece count to 0 when the second checking result is true, thereby obtaining an actual measurement value of the workpiece;
performing a third checking step to check if the GSI value of the workpiece is smaller than or equal to the GSI threshold when the second checking result is false, thereby obtaining a third checking result; and
skipping the measurement of the workpiece performed by the metrology tool when the third checking result is true.

8. The metrology sampling method of claim 7, further comprising:
collecting a plurality of historical measurement values of the historical workpieces corresponding to the sets of historical process data;
performing the model-creation step, further comprising:
building a conjecture model in accordance with a conjecture algorithm by using the sets of historical process data and the historical measurement values;
building a reference model in accordance with a reference prediction algorithm by using the sets of historical process data and the historical measurement values, wherein the conjecture algorithm is different from the reference prediction algorithm; and
computing a RI (Reliance Index) threshold based on a maximal tolerable error limit defined by errors of virtual metrology values obtained from the conjecture mode;
inputting the set of process data into the conjecture model, thereby computing a virtual metrology value of the workpiece;
inputting the set of process data into the reference model, thereby computing a reference prediction value of the workpiece;
calculating an overlap area between the statistical distribution of the virtual metrology value of the workpiece and the statistical distribution of the reference prediction value of the workpiece, thereby generating a RI value of the workpiece;
performing a fourth checking step to check if the RI value of the workpiece is greater than or equal to the RI threshold when the second checking result is false, thereby obtaining a fourth checking result; and
skipping the measurement of the workpiece performed by the metrology tool when the fourth checking result is true.

9. The metrology sampling method of claim 8, further comprising:
performing metrology on the workpiece by using the metrology tool and setting the workpiece count to 0, when the third checking result or the fourth checking result is false, and the GSI values of k workpieces processed before the workpiece all are greater than the GSI threshold or the RI values of k workpieces processed before the workpiece all are smaller than the RI threshold, thereby obtaining the actual measurement value oft the workpiece, wherein k is a positive integer.

10. The metrology sampling method of claim 7, further comprising:
performing a fourth checking step to check if the process tool has been idled for a period of time before the step of increasing the workpiece count by 1, thereby obtaining a fourth checking result; and
performing metrology on the workpiece by using the metrology tool and setting the workpiece count to 0, when the fourth checking result is true, thereby obtaining the actual measurement value of the workpiece.

11. The metrology sampling method of claim 7, further comprising:
performing a fifth checking step to check if the workpiece count is greater than or equal to N+p before the step of performing the first checking step and after the step of increasing the workpiece count by 1, where p is a positive integer; and
performing metrology on the workpiece by using the metrology tool and setting the workpiece count to 0, when the fifth checking result is true, thereby obtaining the actual measurement value of the workpiece.

12. The metrology sampling method of claim 7, further comprising:
performing a fifth checking step to check if a state of the process tool is changed before the step of performing the first checking step and after the step of increasing the workpiece count by 1; and
performing metrology on the workpiece by using the metrology tool and setting the workpiece count to 0, when the fifth checking result is true, thereby obtaining the actual measurement value of the workpiece.

13. The metrology sampling method of claim 7, wherein the GSI model is built in accordance with a Mahalanobis distance algorithm, an Euclidean Distance algorithm, or a centroid method, and the $DQI_X$ model is built in accordance with a principal component analysis (PCA) and an Euclidean distance algorithm, the model-creation step further comprising:
computing the GSI threshold by applying the sets of historical process data in accordance with a cross validation's leave-one-out (LOO) method to; and
computing the $DQI_X$ threshold by using the historical process data and by applying the cross validation's leave-one-out (LOO) method to the $DQI_X$ model.

14. The metrology sampling method of claim 7, wherein the conjecture algorithm and the reference prediction algorithm are respectively a back propagation neural network (BPNN) algorithm, a general regression neural network (GRNN) algorithm, a radial basis function neural network (RBFNN) algorithm, a simple recurrent network (SRN) algorithm, a support vector data description (SVDD) algorithm, a support vector machine (SVM) algorithm, a multiple regression (MR) algorithm, a partial least squares (PLS) algorithm, a nonlinear iterative partial least squares (NIPALS) algorithm or generalized linear models (GLMs).

15. The metrology sampling method of claim 7, wherein the model-creation step further comprises:
building a $DQI_y$ model by using the historical measurement values and the sets of historical process data in accordance with normalized variability (NV) and a clustering algorithm, wherein the clustering algorithm is an adaptive resonance theory 2 (ART2), a fuzzy adaptive resonance theory (Fuzzy ART) or a k-means clustering algorithm; and
computing a $DQI_y$ threshold by applying the sets of historical process data and historical measurement values to the $DQI_y$ model in accordance with the concept of maximal-tolerable variance of similar patterns;
the metrology workpiece sampling step further comprising:
collecting the actual measurement value of the workpiece and the set of process data corresponding to the actual measurement value;
converting the set of process data used for producing the workpiece to a set of z scores;
inputting the set of z scores and the actual measurement value into the $DQI_y$ model, thereby computing a $DQI_y$ value of the actual measurement value of the workpiece; and
requesting measurement for another workpiece which is currently under production when the $DQI_y$ value of the workpiece is greater than the $DQI_y$ threshold.

16. A computer program product stored on a non-transitory tangible computer readable recording medium, which, when executed, performs a metrology sampling method of claim 7.

* * * * *